US010630012B2

(12) United States Patent
Zhao et al.

(10) Patent No.: US 10,630,012 B2
(45) Date of Patent: Apr. 21, 2020

(54) SEMI-AUTOMATIC CONNECTOR FOR FLEXIBLE CIRCUIT

(71) Applicant: QINGDAO BRIGHT MEDICAL MANUFACTURING CO., LTD., Qingdao, Shandong Province (CN)

(72) Inventors: Dezheng Zhao, Qingdao (CN); Yangyang Wan, Qingdao (CN)

(73) Assignee: QINGDAO BRIGHT MEDICAL MANUFACTURING CO., LTD., Qingdao (CN)

( * ) Notice: Subject to any disclaimer, the term of this patent is extended or adjusted under 35 U.S.C. 154(b) by 0 days.

(21) Appl. No.: 16/314,334

(22) PCT Filed: Dec. 30, 2016

(86) PCT No.: PCT/CN2016/113345
§ 371 (c)(1),
(2) Date: Dec. 28, 2018

(87) PCT Pub. No.: WO2018/086228
PCT Pub. Date: May 17, 2018

(65) Prior Publication Data
US 2019/0326694 A1 Oct. 24, 2019

(30) Foreign Application Priority Data

Nov. 10, 2016 (CN) .......................... 2016 1 0989151
Nov. 10, 2016 (CN) ..................... 2016 2 1211656 U

(51) Int. Cl.
*H01R 13/62* (2006.01)
*H01R 12/77* (2011.01)
(Continued)

(52) U.S. Cl.
CPC ......... *H01R 12/774* (2013.01); *H01R 13/506* (2013.01); *H01R 13/6273* (2013.01); *H01R 13/635* (2013.01); *H01R 13/665* (2013.01)

(58) Field of Classification Search
CPC ................ H01R 12/774; H01R 13/665; H01R 13/6273; H01R 13/635; H01R 13/506; H04M 1/21; H01L 41/083; G06F 1/1632
(Continued)

(56) References Cited

U.S. PATENT DOCUMENTS 4,667,155 A * 5/1987 Coiner ............... G01R 1/07328
324/754.14
9,544,408 B2 * 1/2017 Liang ...................... H04M 1/21
(Continued)

FOREIGN PATENT DOCUMENTS

CN 2269650 12/1997
CN 1604397 4/2005
(Continued)

Primary Examiner — Jean F Duverne
(74) Attorney, Agent, or Firm — Jiwen Chen

(57) ABSTRACT

A semi-automatic connector for flexible circuit, comprising a lead wire (6), an upper housing (1), a lower housing (2) and an insert snap portion (4); a button hole (1.1) being opened on the upper housing (1) and a button (3) being disposed in the button hole (1.1); wherein a circuit board (5) is disposed in the lower housing (2) and the top surface of the circuit board (5) provided with elastic sheets (5.1), the circuit board (5) is connected to one end of the lead wire (6); the insert snap portion (4) is disposed above the circuit board (5) with a cavity to receive a flexible circuit pad; the insert snap portion includes two elastic arms (4.1) in parallel and a barb snap (4.1.1) is provided on a free end of each flexible arm (4.1); within the cavity, the flexible circuit pad (8) is being locked as the two barb snaps engaging with recesses (8.1) on the flexible circuit pad (8) and the bottom surface of the flexible circuit pad (8) is in close contact with the elastic (Continued)

sheets (5.1) on the top surface of the circuit board (5); as the button (3) is being pressed downwards, the elastic arms (4.1) are bent until the two barb snaps (4.1.1) on the insert snap portion out of recesses (8.1) of the flexible circuit pad (8). The structure is simple with fewer components and flexible and reliable in connection, which is not easy to detach. The connector has a defibrillation function.

11 Claims, 4 Drawing Sheets

(51) Int. Cl.
*H01R 13/627* (2006.01)
*H01R 13/66* (2006.01)
*H01R 13/506* (2006.01)
*H01R 13/635* (2006.01)

(58) Field of Classification Search
USPC .......................................................... 439/155
See application file for complete search history.

(56) References Cited

U.S. PATENT DOCUMENTS

| | | | |
|---|---|---|---|
| 2008/0002355 A1* | 1/2008 | Carnevali | G06F 1/1632 |
| | | | 361/679.41 |
| 2012/0088388 A1 | 4/2012 | Okano et al. | |
| 2015/0358452 A1* | 12/2015 | Kranz | A61B 5/04087 |
| | | | 455/557 |

FOREIGN PATENT DOCUMENTS

| | | |
|---|---|---|
| CN | 203911135 | 10/2014 |
| CN | 104300250 | 1/2015 |
| CN | 104347982 | 2/2015 |
| CN | 206259520 U | 6/2017 |

* cited by examiner defibrillation high voltage direction defibrillation high voltage direction

SEMI-AUTOMATIC CONNECTOR FOR FLEXIBLE CIRCUIT

This is a U.S. national stage application of PCT Application No. PCT/CN2016/113345 under 35 U.S.C. 371, filed Dec. 30, 2016 in Chinese, claiming priority of Chinese Application No. 2016109891513, filed Nov. 10, 2016 and Chinese Application No. 2016212116569, filed Nov. 10, 2016, all of which are hereby incorporated by reference.

TECHNICAL FIELD

The present invention belongs to the technical field of circuit connector, and relates to an electrode connector configured to connect medical lead wire, in particular to a semi-automatic flexible circuit connector.

BACKGROUND

The miniaturization trend of electronic drives the wide use of flexible circuit, which is known for being able to fold, easy to displace and low in manufacture cost. Most connections between built-in circuits have used Flexible Printed Circuit (FPC) or Flexible Flat Cable (FFC), and the market expects cable to be more lightweight, thin and flexible so that it also begins to be widely used in wire connectors disposed out of device. A flexible circuit typically relies on a board connector that is to insert the flexible circuit into the board connector enabling the flexible circuit to be in contact with a conductive arm via a press lock.

However, the insufficient tensile strength is a major concern of the on-board flexible circuit connector; the connection of the flexible circuit and the conductive arm may be broken or fail if the flexible circuit detaching from the connector as exerting a tension on both ends of the wire, which may reduce the reliability of electronic. Moreover, traditional connector does not allow the repeat pad-in, and it is not convenient for usage and also may lead to waste. In addition, the conventional flexible circuit has other drawbacks of being complicated in structure, hard to manufacture and high in cost.

SUMMARY OF THE INVENTION

One aspect of the present invention is to provide a semi-automatic flexible circuit connector to solve the above-mentioned problems. The semi-automatic flexible circuit is simple in structure with fewer components and able to connect flexibly and reliably.

Another aspect of the present invention is to provide a semi-automatic flexible circuit with a defibrillation function.

The object of the present invention is achieved by the following technical solutions.

A semi-automatic connector for flexible circuit, comprising a lead wire, an upper housing, a lower housing and an insert snap portion; a button hole being opened on the upper housing and a button being disposed in the button hole; wherein a circuit board is disposed in the lower housing and the top surface of the circuit board provided with elastic sheets, the circuit board is connected to one end of the lead wire; the insert snap portion is disposed above the circuit board with a cavity to receive a flexible circuit pad; the insert snap portion includes two elastic arms in parallel and a barb snap is provided on a free end of each flexible arm; within the cavity, the flexible circuit pad is being locked as the two barb snaps engaging with recesses on the flexible circuit pad and the bottom surface of the flexible circuit pad is in close contact with the elastic sheets on the top surface of the circuit board; as the button is being pressed downwards, the elastic arms are bent until the two barb snaps on the insert snap portion out of recesses of the flexible circuit pad.

Further, the insert snap portion is integral and further includes two fixed arms; the fixed arms and the elastic arms are in parallel, and the fixed arms are formed higher than the elastic arms; the cavity is formed between the fixed arms and the elastic arms; protrusions are provided on the top surface of the free ends of the elastic arms, which are close to the barb snaps and extend along the outer side of the barb snaps; button posts are formed on the bottom of the button; as pressing the button, the button posts move downward against the protrusions formed at the free ends of the elastic arms below.

Further two ribs are symmetrically disposed at the top of the insert snap portion where rear ends of the elastic arms are connected to; both of the two ribs are embedded into upper recessed grooves formed on the upper housing as assembled; the insert snap portion further includes two curved fixing strips symmetrically disposed below the two elastic arms; both of the two curved fixing strips are embedded into lower recessed grooves formed on the lower housing as assembled.

In another example of the present disclosure: an insert snap portion comprises an upper insert snap portion and a lower insert snap portion which are independent with each other, the upper insert portion and the lower insert snap portion are in snap fit and a cavity configured to receive a flexible circuit pad is formed between the upper insert portion and the lower insert snap portion; the upper insert snap portion and the bottom of the button are integrally molded; the lower insert snap portion includes two elastic arms and the cavity for receiving the flexible circuit pad is formed between the two elastic arms and the upper insert snap portion; protrusions are provided on the top surface of the free ends of the elastic arms, which are close to the barb snaps and extend along the outer side of the barb snaps; press posts are formed on the bottom of the front ends of the upper insert snap portion; as pressing the button, the press posts move downwards against the protrusions formed at the free ends of the elastic arms below.

Further two connecting rods are arranged in parallel at the rear of the upper insert snap portion; the top surface of each connecting rod is provided with a fixed protrusion; the two fixed protrusions are embedded in an upper recessed groove formed on the upper housing as assembled; a strip groove is formed on the bottom surface of each connecting rod; the lower insert snap portion further includes two fixed bars disposed close to its rear end where fixed ends of the two elastic arms are connected to; a traverse bar is disposed between the two fixed bars; the top surface of each fixed bar is provided with a strip protrusion fitting into the strip groove; the strip protrusions of the upper insert snap portion and the strip groove of the lower insert snap portion are in snap fit, and the fixed bars are embedded into a lower recessed groove formed on the lower housing as assembled.

Further a resistor is provided on the circuit board electronically connected to the lead wire.

Further both sides of the upper housing are provided with upper housing handheld grooves and both sides of the lower housing are provided with lower housing handheld grooves.

Further the insert snap portion is integrally molded.

Further the upper insert snap portion and the button are integrally molded and made of plastic and the lower insert snap portion is independent and made of plastic.

The advantages and positive effects of the present invention over the prior art are:
1. The snap-fit design of the present disclosure is simple and rational with reduced number of components, thereby being easy to manufacture and low in cost. The use of the connector is convenient, flexible and reliable.
2. As the flexible circuit pad inserting into the cavity, recesses thereon are engaged with barb snaps to for locking, thereby avoiding the detachment caused by external tension, in the meanwhile the fixture also ensures the flexible insert pad be in close contact with the elastic sheets on the top of the circuit board; as the button being pressed downwards, the two elastic arms are bent until the barb snaps moving out of the recesses to withdraw the flexible circuit pad conveniently.
3. The anti-slip grooves provided on both sides of the upper and lower housings of increase the frictional force and ensure user could hold the connector firmly.

Figure 1:
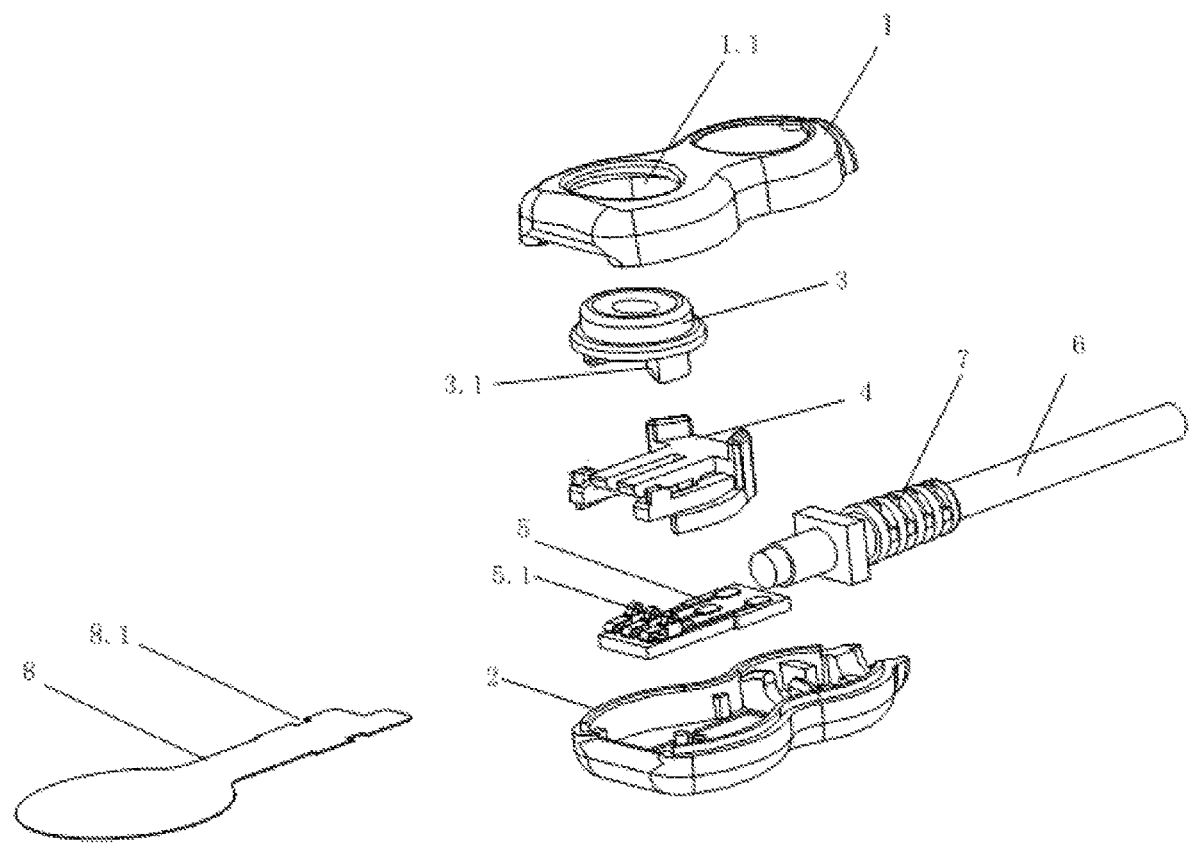
FIG. 1 is a schematic exploded diagram of an embodiment of a semi-automatic flexible circuit connector according to the present invention.
Figure 2:
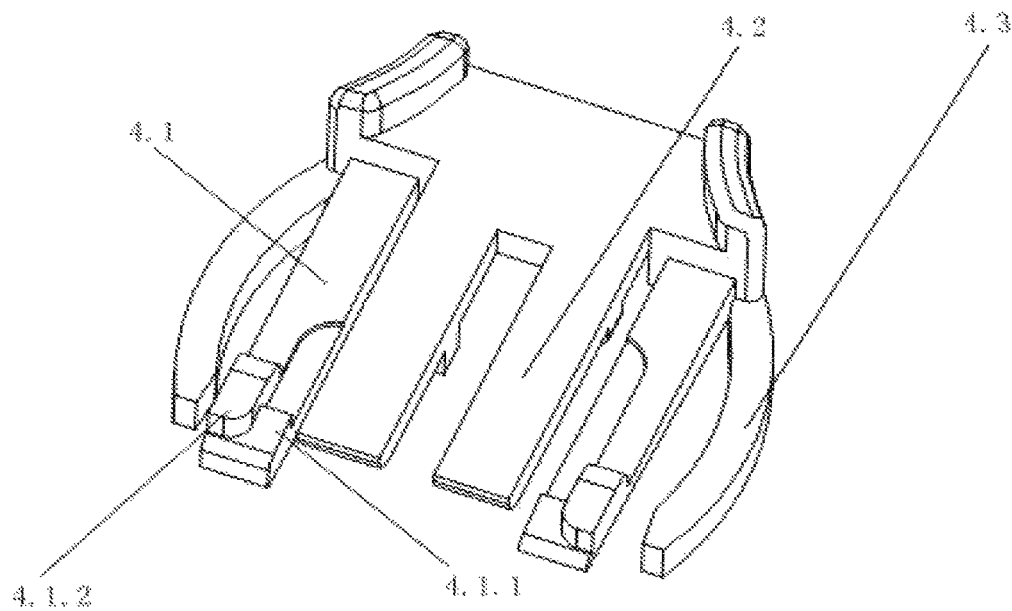
FIG. 2 illustrates an insert snap portion of the semi-automatic flexible circuit connector of FIG. 1.
Figure 3:
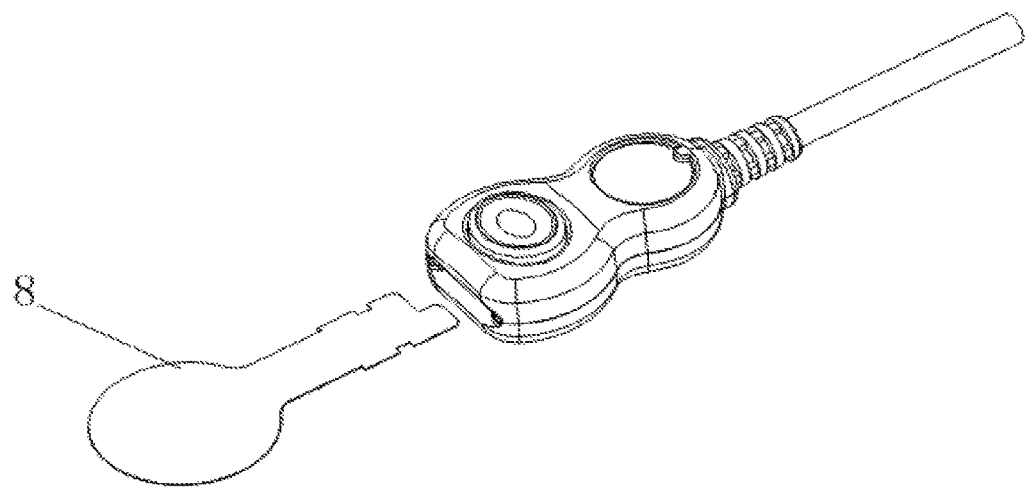
FIG. 3 is a schematic diagram of the semi-automatic flexible circuit connector of FIG. 1 assembled and prepared for receiving a flexible circuit pad.
Figure 4:
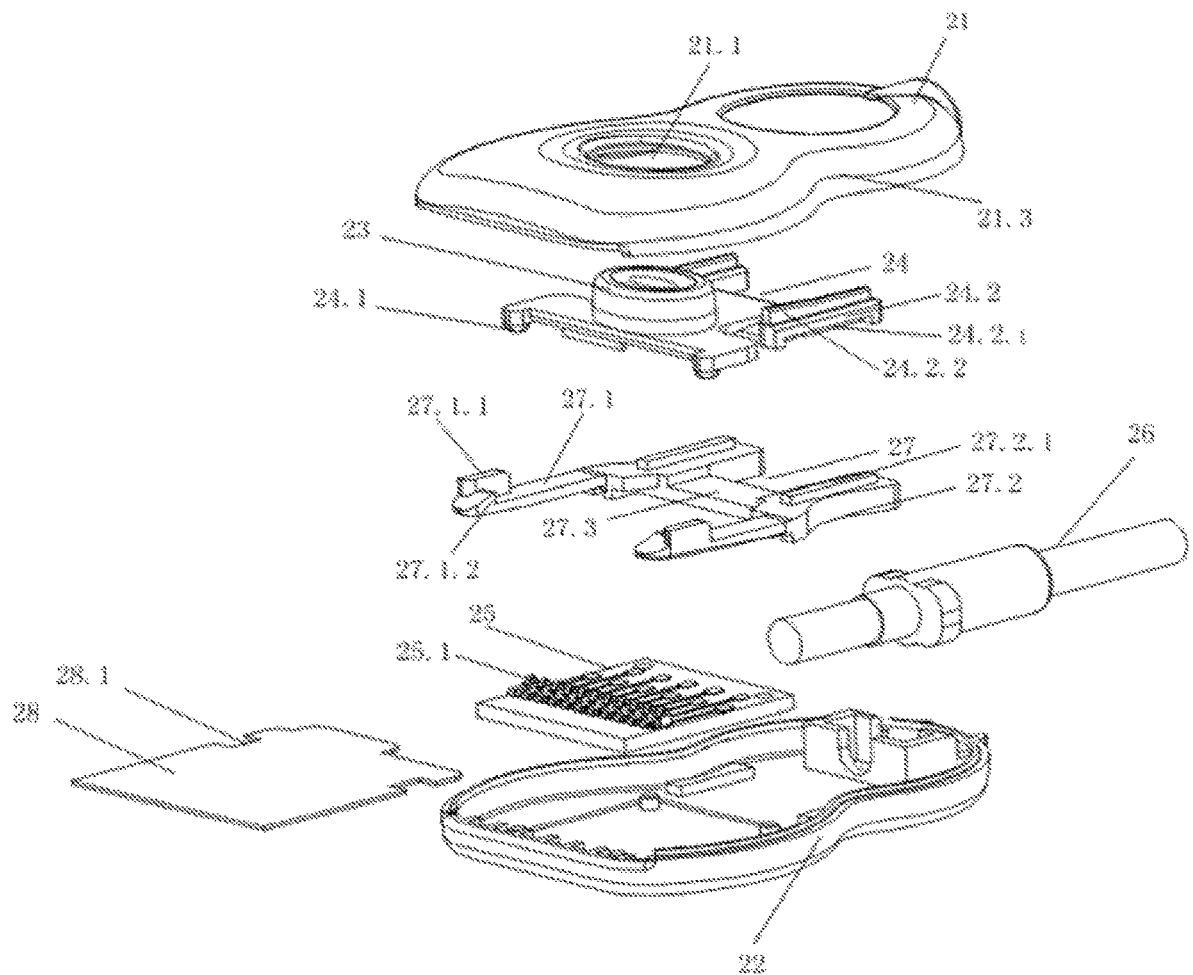
FIG. 4 is a schematic exploded diagram of another embodiment of a semi-automatic flexible circuit connector according to the present invention.
Figure 5:
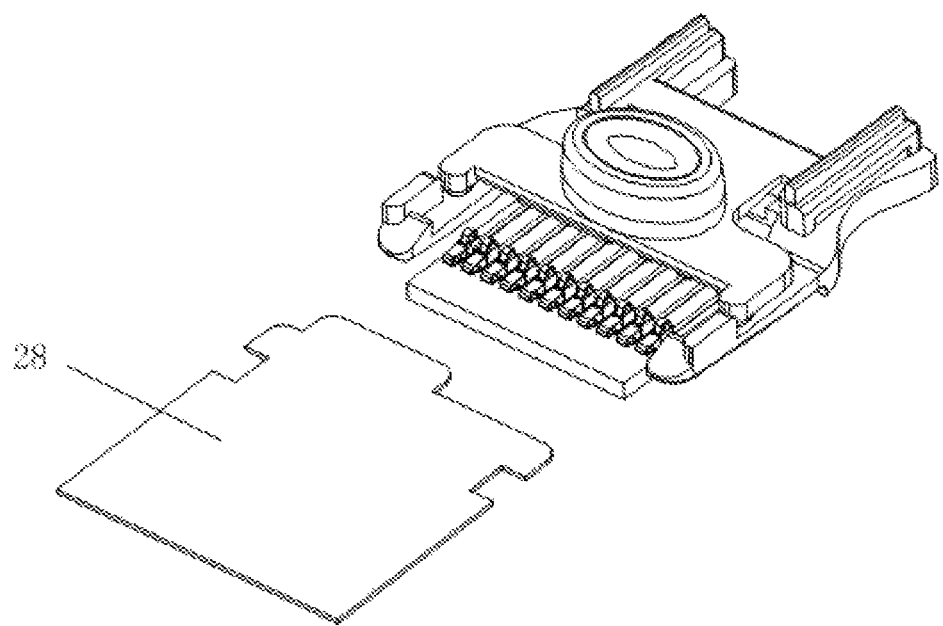
FIG. 5 illustrates a flexible circuit pad of the connector of FIG. 2 before inserting into a recess formed between an upper insert snap portion and a lower insert snap portion in accordance with the present invention.
Figure 6:
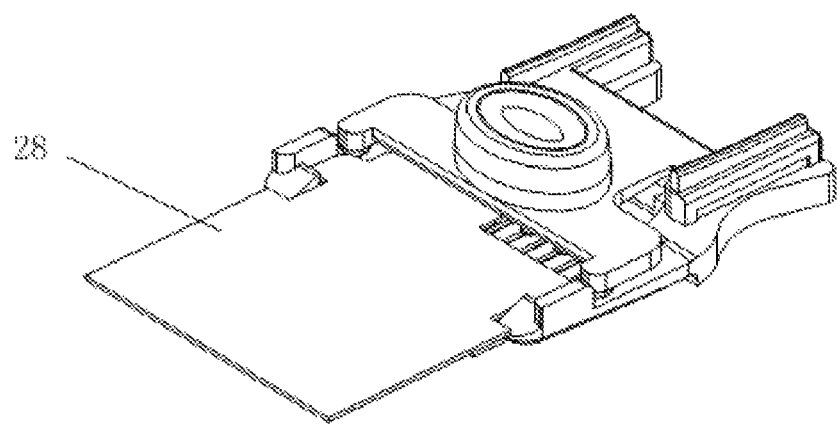
FIG. 6 illustrates a flexible circuit pad of the connector of FIG. 2 after inserting into a recess formed between an upper insert snap portion and a lower insert snap portion in accordance with the present invention.

Wherein in FIG. 1 to FIG. 3 (embodiment 1): 1—upper housing, 1.1—button hole, 2—lower housing, 3—button, 3.1—button post, 4—insert snap portion, 4.1—elastic arm, 4.1.1—barb snap, 4.1.2—protrusion, 4.2—fixed arm, 4.3—curved fixing strip, 4.4—rib, 5—circuit board, 5.1—elastic sheet, 6—lead wire, 7—strain relief, 8—flexible circuit pad, 8.1—recess.

Wherein in FIG. 4 to FIG. 6 (embodiment 2): 21—upper housing, 21.1—button hole, 22—lower housing, 23—button, 24—upper insert snap portion, 24.1—press post, 24.2—connecting rod, 24.2.1—strip groove, 24.2.2—fixed protrusion, 25—circuit board, 25.1—elastic sheet, 26—lead wire, 27—lower insert snap portion, 27.1—elastic arm, 27.1.1—protrusion, 27.1.2—barb snap, 27.2—fixed bar, 27.2.1—strip protrusion, 27.3—traverse bar, 28—flexible circuit pad, 28.1—recess.

DETAILED DESCRIPTION OF EMBODIMENT

Embodiments of the presently disclosed semi-automatic connector for flexible circuit are described herein in detail with reference with the drawings.

Referring to FIGS. 1, 2 and 3, there is shown an example of a semi-automatic connector for flexible circuit having a lead wire 6, a strain relief 7, an upper housing 1, a lower housing 2 and an insert snap portion 4, wherein a button hole 1.1 is opened on the upper housing 1 and a button 3 is disposed in the button hole 1.1. A circuit board 5 is disposed in the lower housing 2 and the top surface of the circuit board 5 is provided with elastic sheets 5.1. The circuit board 5 is connected to one end of the lead wire 6. The insert snap portion 4 is disposed above the circuit board 5. A cavity configured to receive a flexible circuit pad 8 is formed on the insert snap portion 4. The insert snap portion 4 includes two elastic arms 4.1 in parallel and a barb snap 4.1.1 is provided on a free end of each flexible arm 4.1. Connecting the flexible circuit pad 8 to the lead wire 6 electrically may be accomplished by inserting the flexible circuit pad 8 into the cavity formed on the insert snap portion 4 so that the barb snaps 4.1.1 on the free ends of the flexible arms 4.1 may protrude into recesses 8.1 formed on the flexible circuit pad 8 for locking and the bottom surface of the flexible circuit pad 8 is in close contact with the elastic sheets 5.1 on the top surface of the circuit board 5. Releasing the flexible circuit pad 8 may be accomplished by pressing the button 3 to apply pressure on the two elastic arms 4.1 to make them bent downwards, thereby moving the barb snaps 4.1.1 on the insert snap portion 4 out of corresponding recesses 8.1 of the flexible circuit pad 8.

Specifically, the insert snap portion 4 is integrally molded and made of plastic. The insert snap portion 4 further includes two fixed arms 4.2. The fixed arms 4.2 and the elastic arms 4.1 are in parallel, and the fixed arms 4.2 are formed higher than the elastic arms 4.1. The cavity is formed between the fixed arms 4.2 and the elastic arms 4.1 on the insert snap portion 4. Protrusions 4.1.2 are provided on the top surface of the free ends of the elastic arms 4.1, which are close to the barb snaps 4.1.1 and extend along the outer side of the barb snaps 4.1.1. Button posts 3.1 are formed on the bottom of the button 3. As pressing the button 3, the button posts 3.1 move downward against the protrusions 4.1.2 formed at the free ends of the elastic arms 4.1 below so as to bend the elastic arms 4.1 until the barb snaps 4.1.1 moving out of the recesses 8.1 on the flexible circuit pad 8, thereby releasing the flexible circuit pad 8.

Two ribs 4.4 are symmetrically disposed at the top of the insert snap portion 4 where rear ends of the elastic arms 4.1 are connected to. Both of the two ribs 4.4 are embedded into upper recessed grooves formed on the upper housing 1 as assembled for fixing. The insert snap portion 4 further includes two curved fixing strips 4.3 symmetrically disposed below the two elastic arms 4.1. Both of the two curved fixing strips 4.3 are embedded into lower recessed grooves formed on the lower housing 2 as assembled for fixing.

A resistor is provided on the circuit board 5 electronically connected to the lead wire 6 and the resistor value is 1,000 ohms. The resistor enables the semi-automatic flexible circuit to have a defibrillation function.

Both sides of the outer surface of the upper housing 1 are provided with upper housing handheld grooves and both sides of the outer surface of the lower housing 2 are provided with lower housing handheld grooves, so as to maintain a sufficient force between hands and the connector and ensure user could hold the connector firmly.

Referring to FIGS. 4, 5 and 6, there is shown a second example of a semi-automatic connector for flexible circuit having a lead wire 26, an upper housing 21, a lower housing 22 and an insert snap portion, wherein a button hole 21.1 is opened on the upper housing 21 and a button 23 is disposed in the button hole 21.1. A circuit board 25 is disposed in the lower housing 22 and the top surface of the circuit board 25 is provided with elastic sheets 25.1. The circuit board 25 is connected to one end of the lead wire 26. The insert snap portion is disposed above the circuit board 25 and comprises an upper insert snap portion 24 and a lower insert snap portion 27. The upper insert portion 24 and the lower insert snap portion 27 are in snap fit and a cavity configured to receive a flexible circuit pad 28 is formed between the upper insert portion 24 and the lower insert snap portion 27.

Specifically, the upper insert snap portion 24 and the bottom of the button 23 are integrally molded. The lower insert snap portion 27 includes two elastic arms 27.1 in parallel and the cavity for receiving the flexible circuit pad is formed between the two elastic arms 21.1 and the upper insert snap portion 24. A barb snap 27.1.2 is provided on a free end of each flexible arm 27.1. Protrusions 27.1.1 are provided on the top surface of the free ends of the elastic arms 27.1, which are close to the barb snaps 27.1.2 and extend along the outer side of the barb snaps 27.1.2. Press posts 24.1 are formed on the bottom of the front ends of the upper insert snap portion 24. Connecting the flexible circuit pad 28 to the lead wire 26 electrically may be accomplished by inserting the flexible circuit pad 28 into the cavity so that the barb snaps 27.1.2 may protrude into recesses 28.1 formed on the flexible circuit pad 28 for locking and the bottom surface of the flexible circuit pad 28 is in close contact with the elastic sheets 25.1 on the top surface of the circuit board 5. Releasing the flexible circuit pad 8 may be accomplished by pressing the button 23 to push the press posts 24.1 against the protrusions 27.1.1 formed at the free ends of the elastic arms 27.1 below so as to bend the elastic arms 27.1 until the barb snaps 27.1.2 of the elastic arms 27.1 moving out of the recesses 8.1 on the flexible circuit pad 8, and then withdrawing the flexible circuit pad 28.

Two connecting rods 24.2 are arranged in parallel at the rear of the upper insert snap portion 24. The top surface of each connecting rod 24.2 is provided with a fixed protrusion 24.2.2. The two fixed protrusions 24.2.2 are embedded in an upper recessed groove formed on the upper housing 21 as assembled. A strip groove 24.2.1 is formed on the bottom surface of each connecting rod 24.2. The lower insert snap portion 27 further includes two fixed bars 27.2 disposed close to its rear end where fixed ends of the two elastic arms 27.1 are connected to. A traverse bar 27.3 is disposed between the two fixed bars 27.2. The top surface of each fixed bar 27.2 is provided with a strip protrusion 27.2.1 fitting into the strip groove 24.2.1. The strip protrusions 27.2.1 of the upper insert snap portion 24 and the strip groove 24.2.1 of the lower insert snap portion 27 are in snap fit, and the fixed bars 27.2 are embedded into a lower recessed groove formed on the lower housing 22 as assembled.

The upper insert snap portion 24 and the button 23 are integrally molded and made of plastic and the lower insert snap portion 27 is a separated molded plastic component.

A resistor is provided on the circuit board 5 electronically connected to the lead wire 6 and the resistor value is 1,000 ohms. The resistor enables the semi-automatic flexible circuit to have a defibrillation function.

Both sides of the outer surface of the upper housing 21 are provided with upper housing handheld grooves and both sides of the outer surface of the lower housing 22 are provided with lower housing handheld grooves, so as to maintain a sufficient force between hands and the connector and ensure user could hold the connector firmly.

Figure 7:
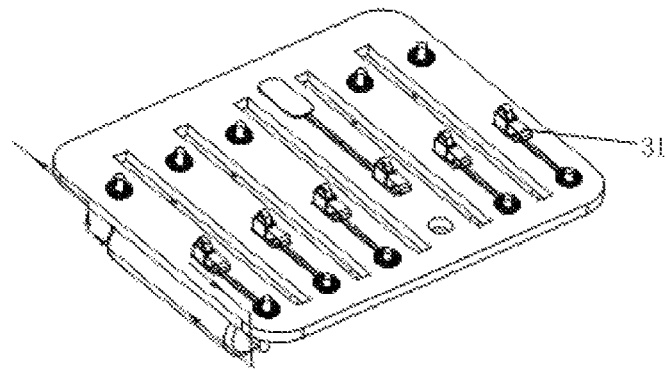
FIG. 7 is a perspective view showing a top surface of a circuit board in an example of a semi-automatic flexible circuit connector according to the present invention.
Figure 8:
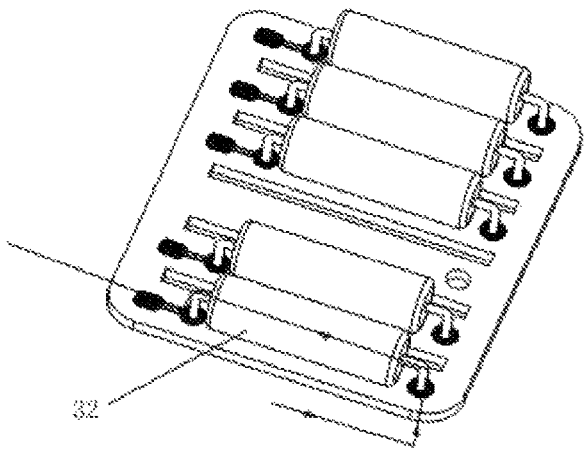
FIG. 8 is a perspective view showing a bottom surface of a circuit board in an example of a semi-automatic flexible circuit connector according to the present invention.

As shown in FIG. 7 and FIG. 8, there is shown an example of a circuit board in accordance with the present invention, in which a defibrillation resistor 32 is provided in a circuit electronically connected to the lead wire, and the defibrillation resistor 32 value is 1,000 ohms. The defibrillation resistor 32 is disposed on the bottom surface of the circuit board, and arrows in FIG. 7 and FIG. 8 show directions of defibrillation high voltage indicating voltage drop as flowing through the resistor. Referring to FIG. 7, elastic sheets are provided on contacts 31 to be in contact with the flexible circuit pad.

It will be understood that various modifications may be made to the embodiments disclosed herein. Further variations of the above-disclosed and other features and functions, or alternatives thereof, may be desirably combined into many other different systems, instruments and applications. Various presently unforeseen or unanticipated alternatives, modifications, variations or improvements therein may be subsequently made by those skilled in the art, which are also intended to be encompassed by the following claims.

The invention claimed is:

1. A semi-automatic connector for a flexible circuit, comprising a lead wire, an upper housing, a lower housing and an insert snap portion; a button hole being opened on the upper housing and a button being disposed in the button hole; wherein a circuit board is disposed in the lower housing and the top surface of the circuit board provided with elastic sheets, the circuit board is connected to one end of the lead wire; the insert snap portion is disposed above the circuit board with a cavity to receive a flexible circuit pad; the insert snap portion includes two elastic arms in parallel and a barb snap is provided on a free end of each flexible arm; within the cavity, the flexible circuit pad is being locked as the two barb snaps engaging with recesses on the flexible circuit pad and the bottom surface of the flexible circuit pad is in close contact with the elastic sheets on the top surface of the circuit board; as the button is being pressed downwards, the elastic arms are bent until the two barb snaps on the insert snap portion out of recesses of the flexible circuit pad.

2. The semi-automatic connector for the flexible circuit according to claim 1, wherein the insert snap portion is integral and further includes two fixed arms; the fixed arms and the elastic arms are in parallel, and the fixed arms are formed higher than the elastic arms; the cavity is formed between the fixed arms and the elastic arms; protrusions are provided on the top surface of the free ends of the elastic arms, which are close to the barb snaps and extend along the outer side of the barb snaps; button posts are formed on the bottom of the button 3; as pressing the button, the button posts move downward against the protrusions formed at the free ends of the elastic arms below.

3. The semi-automatic connector for the flexible circuit according to claim 2, wherein two ribs are symmetrically disposed at the top of the insert snap portion where rear ends of the elastic arms are connected to; both of the two ribs are embedded into upper recessed grooves formed on the upper housing as assembled; the insert snap portion further includes two curved fixing strips symmetrically disposed below the two elastic arms; both of the two curved fixing strips are embedded into lower recessed grooves formed on the lower housing as assembled.

4. The semi-automatic connector for the flexible circuit according to claim 1, wherein the insert snap portion comprises an upper insert snap portion and a lower insert snap portion, the upper insert portion and the lower insert snap portion are in snap fit and a cavity configured to receive a flexible circuit pad is formed between the upper insert portion and the lower insert snap portion; the upper insert snap portion and the bottom of the button are integrally molded; the lower insert snap portion includes the two elastic arms and the cavity for receiving the flexible circuit pad is formed between the two elastic arms and the upper insert snap portion; protrusions are provided on the top surface of the free ends of the elastic arms, which are close to the barb snaps and extend along the outer side of the barb snaps; press posts are formed on the bottom of the front ends of the upper insert snap portion; as pressing the button, the press posts move downward against the protrusions formed at the free ends of the elastic arms below.

5. The semi-automatic connector for the flexible circuit according to claim 4, wherein two connecting rods are arranged in parallel at the rear of the upper insert snap portion; the top surface of each connecting rod is provided with a fixed protrusion; the two fixed protrusions are embedded in an upper recessed groove formed on the upper housing as assembled; a strip groove is formed on the bottom surface of each connecting rod; the lower insert snap portion further includes two fixed bars disposed close to its rear end where fixed ends of the two elastic arms are connected to; a traverse bar is disposed between the two fixed bars; the top surface of each fixed bar is provided with a strip protrusion fitting into the strip groove; the strip protrusions of the upper insert snap portion and the strip groove of the lower insert snap portion are in snap fit, and the fixed bars are embedded into a lower recessed groove formed on the lower housing as assembled.

6. The semi-automatic connector for the flexible circuit according to claim 1, wherein a resistor is provided on the circuit board electronically connected to the lead wire.

7. The semi-automatic connector for the flexible circuit according to claim 1, wherein both sides of the upper housing are provided with upper housing handheld grooves and both sides of the lower housing are provided with lower housing handheld grooves.

8. The semi-automatic connector for the flexible circuit according to claim 6, wherein both sides of the upper housing are provided with upper housing handheld grooves and both sides of the lower housing are provided with lower housing handheld grooves.

9. The semi-automatic connector for the flexible circuit according to claim 1, wherein the insert snap portion is integrally molded.

10. The semi-automatic connector for the flexible circuit according to claim 4, wherein the upper insert snap portion and the button are integrally molded and made of plastic and the lower insert snap portion is independent and made of plastic.

11. The semi-automatic connector for the flexible circuit according to claim 5, wherein the upper insert snap portion and the button are integrally molded and made of plastic and the lower insert snap portion is independent and made of plastic.

* * * * *